US012618068B2

(12) United States Patent
Lin et al.

(10) Patent No.: US 12,618,068 B2
(45) Date of Patent: *May 5, 2026

(54) REPLICASE CYCLING REACTION (RCR) AND THE RELATED SamRNA DESIGNS THEREOF

(71) Applicants: Shi-Lung Lin, Arcadia, CA (US); Sam Lin, Arcadia, CA (US); Chun-Hung Lin, Taipei (TW)

(72) Inventors: Shi-Lung Lin, Arcadia, CA (US); Sam Lin, Arcadia, CA (US); Chun-Hung Lin, Taipei (TW)

( * ) Notice: Subject to any disclaimer, the term of this patent is extended or adjusted under 35 U.S.C. 154(b) by 704 days.

This patent is subject to a terminal disclaimer.

(21) Appl. No.: 18/156,231

(22) Filed: Jan. 18, 2023

(65) Prior Publication Data

US 2023/0295627 A1 Sep. 21, 2023

Related U.S. Application Data

(63) Continuation-in-part of application No. 17/489,357, filed on Sep. 29, 2021, now Pat. No. 12,570,977, and a continuation-in-part of application No. 17/648,336, filed on Jan. 19, 2022, and a continuation-in-part of application No. 17/648,340, filed on Jan. 19, 2022, now abandoned.

(60) Provisional application No. 63/302,163, filed on Jan. 24, 2022, provisional application No. 63/338,881, filed on May 5, 2022, provisional application No. 63/429,150, filed on Dec. 1, 2022.

(51) Int. Cl.

| | |
|---|---|
| *C12N 15/11* | (2006.01) |
| *C12N 9/12* | (2006.01) |
| *C12N 15/113* | (2010.01) |
| *C12Q 1/686* | (2018.01) |

(52) U.S. Cl.
CPC ............ *C12N 15/113* (2013.01); *C12N 9/127* (2013.01); *C12Q 1/686* (2013.01); *C12N 2310/141* (2013.01); *C12Y 207/07048* (2013.01)

(58) Field of Classification Search
None
See application file for complete search history.

(56) References Cited

U.S. PATENT DOCUMENTS

| | | |
|---|---|---|
| 7,662,791 B2 | 2/2010 | Lin et al. |
| 8,080,652 B2 | 12/2011 | Lin et al. |
| 8,372,969 B2 | 2/2013 | Ying et al. |
| 8,609,831 B2 | 12/2013 | Lin et al. |
| 2023/0242958 A1 | 8/2023 | Lin et al. |

FOREIGN PATENT DOCUMENTS

WO 2002/092774 A2 11/2002

OTHER PUBLICATIONS

Lin, et al., cDNA library construction using in vitro transcriptional amplification, Methods Mol Biol., 2003;221:93-101.

Ahn, et al., Biochemical characterization of a recombinant SARS coronavirus nsp12 RNA-dependent RNA polymerase capable of copying viral RNA templates, Arch Virol., Nov. 2012; 157(11):2095-104.

Bloom, et al., Self-amplifying RNA vaccines for infectious diseases. Gene Ther, 2020;28:117-129.

Mcdowell, et al., Determination of intrinsic transcription termination efficiency by RNA polymerase elongation rate. Science 2, 1994;66:822-825.

Aasen, et al., Isolation and cultivation of human keratinocytes from skin or plucked hair for the generation of Induced pluripotent stem cells., Nat. Protocols, 2010;5:371-382.

Lin, et al., Mir-302 reprograms human skin cancer cells into a pluripotent ES-cell-like state. RNA, 2008; 14:2115-2124.

Lin, et al., Regulation of somatic cell reprogramming through inducible mir-302 expression. Nucleic Acids Res., 2011;39:1054-1065.

Takahashi, et al., Induction of pluripotent stem cells from mouse embryonic and adult fibroblast cultures by defined factors. Cell, 2006;126:663-676.

Hillen, et al., Structure of replicating SARS-CoV-2 polymerase. Nature, 2020;584;154-156.

*Primary Examiner* — Ekaterina Poliakova-Georgantas
(74) *Attorney, Agent, or Firm* — ArentFox Schiff LLP

(57) ABSTRACT

This invention generally relates to a novel composition of RNA/mRNA medicines as well as vaccines produced by using replicase- and/or RNA-dependent RNA polymerase (RdRp)-mediated RNA cycling reaction (RCR). The present invention is useful for developing a variety of self-amplifying RNA/mRNA (samRNA) medicines and vaccines containing at least a replicase/RdRp-binding site in the 5'- or 3'-end, or both, of any desired RNA molecule, including but not limited to antisense RNA (aRNA), small interfering RNA (siRNA), short hairpin RNA (shRNA), microRNA (miRNA)/miRNA precursor, long non-coding RNA (lnRNA) and mRNA. These RNA molecules can be either in single-stranded or in double-stranded, or mixed, conformation. The samRNA so obtained is useful not only for producing RNA-based vaccines and/or medicines but also for generating the mRNA-associated proteins, peptides, and/ or antibodies under a proper in-vitro or in-cell translation condition. The replicase/RdRp-binding sites used in samRNA are derived or modified from coronaviral (e.g. COVID-19) and/or hepatitis C viral (HCV) RNA-dependent RNA polymerases (RdRp) in either single-stranded or double-stranded compositions.

14 Claims, 6 Drawing Sheets

Specification includes a Sequence Listing.

← RCR-ready cDNA
   templates

RCR-ready RNA
templates and ←
RCR-amplified RNAs
(*i.e.* COVID S2 mRNA)

hematoxylin stain
(background)                    COVID S2 protein

REPLICASE CYCLING REACTION (RCR) AND THE RELATED SamRNA DESIGNS THEREOF

PRIORITY

The present invention claims priority to U.S. Provisional Patent Applications No. 63/302,163 filed on Jan. 24, 2022, and No. 63/338,881 filed on May 5, 2022, both of which are entitled "Novel Replicase Cycling Reaction (RCR)". The present invention also claims priority to U.S. Provisional Patent Application No. 63/429,150 filed on Dec. 1, 2022, which is entitled "Novel Replicase Cycling Reaction (RCR) and The Related SamRNA Designs Thereof". Additionally, the present application is a continuation-in-part application of the U.S. patent application Ser. No. 17/489,357 filed on Sep. 29, 2021, which is entitled "Novel mRNA Composition and Production Method for Use in Anti-Viral and Anti-Cancer Vaccines". The present application is also a continuation-in-part application of the U.S. patent application Ser. No. 17/648,336 filed on Jan. 19, 2022, which is entitled "Novel Replicase Cycling Reaction (RCR)". Moreover, the present application is a continuation-in-part application of the U.S. patent application Ser. No. 17/648,340 filed on Jan. 19, 2022, which is entitled "Novel RNA Composition and Production Method for Use in iPS Cell Generation". All aforementioned six prior patent applications are hereby incorporated by reference as if fully set forth herein.

REFERENCE TO AN ELECTRONIC SEQUENCE LISTING

The contents of the electronic sequence listing (027706-00057-Sequence Listing.xml; Size: 6,879 bytes; and Date of Creation: Jan. 18, 2023) are herein incorporated by reference in its entirety.

FIELD OF INVENTION

This invention generally relates to a novel non-replicon-based self-amplifying RNA/mRNA (samRNA) composition capable of being produced by using RNA replicase- and/or RNA-dependent RNA polymerase (RdRp)-mediated cycling reaction (RCR). The present invention is useful for designing and developing a variety of self-amplifying RNA/mRNA (samRNA) medicines as well as vaccines containing at least a replicase/RdRp-binding site in the 5'-end or 3'-end, or both, of any desired RNA molecule, including but not limited to antisense RNA (aRNA), small interfering RNA (siRNA), short hairpin RNA (shRNA), microRNA (miRNA)/miRNA precursor (pre-miRNA), long noncoding RNA (lnRNA), and messenger RNA (mRNA). The conformation of these desired RNA molecules can be either single strand or double strand, or a mixture (like shRNA or pre-miRNA) thereof. The samRNA so obtained is useful not only for producing RNA/mRNA-based vaccines and medicines but also for generating the mRNA-associated proteins, peptides, and/or antibodies under a proper in-vitro or in-cell translation condition. The replicase/RdRp-binding sites used in samRNA constructs are derived or modified from coronaviral (e.g. COVID-19) and/or hepatitis C viral (HCV) RdRp-binding sites in either single-stranded or double-stranded DNA/RNA compositions.

BACKGROUND

Prior polymerase chain reaction (PCR) is a method using thermostable DNA polymerases to amplify double-stranded DNA sequences from DNA templates, no involvement of any RNA material. Unlike PCR, newly invented RNA replicase/RdRp-mediated cycling reaction (RCR) uses RNA-dependent RNA polymerases (RdRp) to amplify single-stranded and/or double-stranded RNA/mRNA sequences from desired samRNA platform templates, no requirement of any DNA template. Clearly, PCR and RCR are very different methods and thus not comparable to each other. Hence, previous PCR studies are not related to RCR. As a result, the RCR-amplified RNA/mRNA (samRNA) products are herein neither related nor comparable to the PCR products as well.

Lin et al. first reported RCR in year 2002 (WO2002/092774 to Lin). Lin had found that using a special design of 5'-cap-capture primers can trigger some viral and/or bacteriophage replicase-mediated RNA amplification from single-stranded or double-stranded RNA templates. This prior RCR mechanism may mimic the replication/amplification mechanisms of certain RNA viruses or bacteriophages, but not representing all kinds of RNA viruses. Particularly, the requirement of specific 5'-cap-capture primers limits its use because many RNA species do not carry 5'-cap molecules. Also, the linked 5'-cap-capture molecules may contaminate the resulting RNA products. For serving as RNA/mRNA medicines or vaccines, this contamination is problematic because removal of the 5'-cap-capture molecules from the RNA products is tedious and may cause RNA degradation. Hence, a new RCR method without using any 5'-cap-capture primer or molecule is highly desirable.

In year 2012, Ahn et al reported a pair of 5'- and 3'-end RNA-dependent RNA polymerase (RdRp) binding sites isolated from severe acute respiratory syndrome coronavirus (SARS-CoV) (Ahn et al., Arch. Virol. 157:2095-2104, 2012). This pair of SARS-CoV RdRp-binding sites consists of minimal 36-37-nucleotide (nt)-long hairpin-like stem-loop RNA structures, which are however not compatible with PCR due to their lengthy and highly structured sequences. In order to prevent replicon/plasmid-based template preparation, a combined methodology of polymerase chain reaction-in vitro transcription (PCR-IVT) is often used to generate RdRp-amplifiable RNA templates, or called self-amplifying RNAs/mRNAs (samRNAs) (FIGS. 1 and 2; U.S. Pat. Nos. 7,662,791, 8,080,652, 8,372,969, and 8,609,831 to Lin; Lin et al., *Methods Mol Biol.* 221:93-101, 2003). Unfortunately, Ahn's method can not be used with prior PCR-IVT methods because the lengthy and highly structured SARS-CoV RdRp-binding sites actually hinder both PCR and RCR. Based on prior studies, it has been noted that any large stem-loop structure (>7-9-bp) can not be placed in the 5'-end of a PCR or RCR template. As a result, the resulting RNA/mRNA products can not be used in RCR-mediated amplification; hence, they are not RCR-amplifiable samRNAs. Moreover, Ahn's finding is limited only to SARS-CoV RdRp, not else. For COVID-19 or HCV RdRp, Ahn's finding is not useful because the key sequences and structures of COVID-19 and SARS-CoV RdRp are different.

Recently, several RCR-like methodologies and their related samRNA designs have been reviewed by Bloom et al. (*Gene Therapy* 28:117-129, 2021), using alphaviral RdRp and its only one found 3'-binding/recognition site, a ~19-nt-long 3'-conserved sequence element called 3'-CSE. Yet, neither concept nor practical detail of any RCR protocol was provided due to lack of any 5'-end binding/recognition site. Although Bloom's review methods may not use any 5'-cap-capture primer, the proposed 3'-CSE is too long and too structural to be incorporated into a PCR primer. Based on prior studies, this 3'-CSE can not be placed in the 5'-end of a PCR or RCR template. As a result, RNA/mRNA containing the 3'-CSE is not compatible with either PCR-IVT or RCR methods. Alternatively, those prior methods usually use vector (e.g. replicon)/plasmid-based amplification to produce 3'-CSE-containing RNAs/mRNAs in the transfected cells or bacteria. Interestingly, the resulting 3'-CSE-containing RNAs/mRNAs (described as a kind of samRNAs in Bloom's review) however have never been proved to be amplifiable using RCR or any kind of similar methods. Because replicon-based samRNA technologies use whole modified RNA virus genomes, but not their specific RdRp-binding sites (mostly still unknown, such as those of flaviviruses and picornaviruses), it is obvious that those prior replicon-based technologies are different from and thus not comparable to the present invention using specific viral RdRp-binding sites. Also, because 3'-CSE is a lengthy and highly structured sequence, it hinders RNA transcription using prokaryotic RNA polymerases (McDowell et al., Science 266:822-825, 1994) and hence the resulting RNA products may not be efficiently amplified in traditional IVT or PCR-IVT methods. More problematically, 3'-CSE is only recognized by alphaviral RdRp, which contains at least four distinct subunits and is not commercially available, resulting in further hindering the development of its related RCR technology. Given that the properties of different viral replicase/RdRp species are different, it is desirable to search and utilize another kind of replicase/RdRp with a more compact and less structural binding stie for overcoming the problems of those prior samRNA-like designs.

Logically, a real samRNA design should be able to be amplified by RCR methods in vitro. However, all prior studies and designs using either alphaviral or SARS-CoV RdRp-binding sites fail to prove or achieve this key point due to many intrinsic and technical problems. In view of these many problems of previous RCR or RCR-like methods and their related samRNA-like designs, it is herein highly desirable to develop a novel samRNA composition not only with more compact and less structural replicase/RdRp-binding sites but also without containing any 5'-cap-capture primer, so as to really achieve high-throughput RNA/mRNA amplification as well as production using RCR technologies.

SUMMARY OF THE INVENTION

The principle of the present invention is relied on the incorporation of at least a specific coronaviral (e.g. COVID-19) or hepatitis C viral (HCV) replicase/RdRp-binding (recognition) site into the 5'-end or 3'-end, or both, of desired RNA templates, leading to the cycling amplification of either the sense (+) strands or antisense (−) strands, or both, of the desired RNA sequences. The resulting self-amplifying RNAs/mRNAs are called samRNA, which can be further served as a samRNA platform template for next cycle of RCR amplification, repeatedly. Since the present invention uses specific precise replicase/RdRp-binding sites, not modified viral genomes, for inducing RCR amplification of desired samRNA sequences, all prior replicon-based self-replicating RNA (saRNA) designs and methods are herein different from and not comparable to the present invention.

In RCR, the defined replicase/RdRp-binding sites are served as a promoter-like and/or enhancer-like motif for initiating replicase/RdRp activities. As shown in FIG. 2, after incorporation of at least a replicase/RdRp-binding site into the 5'-end and 3'-end of a desired RNA/mRNA template, the desired RNA/mRNA sequences can be amplified from about 10-15 to over 1000 folds in each cycle of replicase/RdRp cycling reaction (RCR). In RCR, the sense-strand (+) RNA sequences are used as templates for amplifying the antisense [or complementary (−)] strands of the sense-strand RNAs, while the resulting antisense-strand (−) RNA sequences are then in turns served as templates for amplifying the sense-strand (+) RNAs. Hence, both of sense-strand (+) and antisense-strand (−) RNAs can be served as templates for desired RNA/mRNA amplification in RCR. Also, all the resulting RNA products so obtained are self-amplifying RNAs/mRNAs (samRNAs) using RCR. Based on this proof-of-concept principle of the present invention, it is conceivable that the same RCR protocol may use different kinds of viral replicase and/or RdRp enzymes with their corresponding binding sites to design and amplify various samRNAs.

Each cycle of RCR can provide an about 10-15- to over 1000-fold RNA amplification rate in a defined time period, depending on not only the length and structural complexity of the desired samRNA sequence(s) but also the combination of used replicase/RdRp-binding sites. Different replicase/RdRp-binding sites provide different RNA amplification rates, which may be very different. Using a combination of strong and weak binding sites in the different ends of samRNA, we can selectively amplify more of either the sense-strand (+) or antisense-strand (−), or both, of samRNA with a high purity ratio (maximally 14/15 to >999/1000 purity). Notably, the desired samRNA sequences and templates in RCR can be more than one kind and the resulting samRNA products can be in either single- or double-strand conformation.

To prepare RCR-amplifiable (or RCR-ready) samRNA platform templates, we preferably use reverse transcription-polymerase chain reaction (RT-PCR) or only PCR to incorporate at least a coronaviral (e.g. COVID-19) and/or HCV replicase/RdRp-binding site into the 5'- or 3'-ends, or both, of the complementary DNAs (cDNA) of desired RNA/mRNA sequences. In our design, at least a replicase/RdRp-binding site is synthetically embedded in each of the PCR primers (called RCR-ready PCR primers) and hence the cDNAs of the first samRNA platform templates are formed after RT-PCR or PCR with the designed replicase/RdRp-binding sites incorporated in the 5'- or 3'-ends thereof, or both. Alternatively, the resulting cDNAs can be cloned into a plasmid or viral vector for further IVT reaction and/or storage preservation. After obtaining the cDNAs of RCR-ready samRNA platform templates, an IVT reaction is then performed to produce the first strands of samRNA templates from the cDNAs. After further purification to remove cDNAs, the resulting samRNA templates can be used in RCR to repeatedly amplify and produce the desired RNA/mRNA (samRNA) sequences. Alternatively, in another way of real practice, since the IVT and RCR can also be performed simultaneously under our designed buffer conditions, the replicase/RdRp-binding site-incorporated cDNAs (called RCR-ready cDNA templates) can also be served as a starting material for amplifying the desired samRNA sequences in a combined IVT-RCR reaction.

Previously from various COVID-19 strains and HCV genomes, we had isolated and further modified several conserved homologs of replicase/RdRp-binding sites, including 5'- and 3'-end RdRp-binding sites, respectively. As shown in our prior studies as well as in the claimed priority invention U.S. patent application Ser. Nos. 17/648,336 and 17/648,340, these identified RdRp-binding sites share high similarity and compatibility to each other. In details, the 5'-end RdRp-binding site contains at least a consensus sequence homologous to either 5'-AU(G/C)(U/-)G(A/U)-3' (i.e. 5'-AUSUGW-3'; SEQ ID NO:1) or 5'-U(C/-)(U/A)C(U/

C)(U/A)A-3' (i.e. 5'-UCWCYWA-3'; SEQ ID NO:2), or both, while the 3'-end RdRp-binding site contains at least a consensus sequence homologous to either 5'-(U/A)C(A/-)(C/G)AU-3' (i.e. 5'-WCASAU-3'; SEQ ID NO:3) or 5'-U(A/U)(A/G)G(A/U)(G/-)A-3' (i.e. 5'-UWRGWR-3'; SEQ ID NO:4), or both. Preferably, the 5'-end RdRp-binding site contains at least a sequence of 5'-AUCUGU-3' (SEQ ID NO:5), 5'-UCUCUAA-3' (SEQ ID NO:6), 5'-UCUCCUA-3' (SEQ ID NO:7), and/or 5'-UUCAA-3' (SEQ ID NO:8), or a combination thereof, while the 3'-end RdRp-binding site contains at least a sequence of 5'-ACAGAU-3' (SEQ ID NO:9), 5'-UUAGAGA-3' (SEQ ID NO:10), 5'-UAGGAGA-3' (SEQ ID NO:11), and/or 5'-UUGAA-3' (SEQ ID NO:12), or a combination thereof. Also, these RdRp-binding sites can be used together with each other to form a combination, as described in our priority U.S. patent application Ser. Nos. 17/648,336 and 17/648,340. For example, to enhancing RdRp binding efficiency, SEQ ID NO:8 and SEQ ID NO:12 are usually used with other RdRp-binding sites. Notably, in all these identified RdRp-binding sites, the sequence contents of uracil (U) and thymine (T) are exchangeable, depending on different cDNA template and/or RNA designs.

Due to our novel modifications, the new RdRp-binding sites of this invention can achieve multiple cycles of RCR-mediated samRNA amplification, whereas the previously reported Ahn's and Bloom's large stem-loop binding sites only provide 3'-end RNA extension of one strand, but not cycling amplification of both strands because the reported large stem-loop structures can not be placed in the 5'-end of RCR-ready samRNA platform templates (usually defined as the sense (+) strand), of which the position is complementary to the 3'-end of the resulting synthesized RNAs (usually defined as the antisense (−) strand). It is noted that the resulting antisense (−) strand RNAs will serve as new templates for the next cycle amplification of the sense-strand (+) RNAs. Since RdRp starts transcription from the 3'- to 5'-orientation (in the complementary direction) of a samRNA template, any large (>7-9-bp) stem-loop structure in the 3'-end of the resulting synthesized (−) RNAs (equivalent to the 5'-end of the desired (+) RNAs) will hinder the initiation of next cycle RNA synthesis of samRNAs.

Also, for facilitating RCR-ready PCR primer designs, the uridine/uracil (U) contents of these RdRp-binding sites can be replaced by thymidine (dT) and/or deoxyuridine (dU) in the primers. Moreover, for enhancing RNA stability, the uridine/uracil (U) contents of these RdRp-binding sites can be further replaced by pseudouridine, 5-methyluridine, 5-methoxyuridine, or any other proper modified nucleotide analog during IVT and/or RCR. For facilitating protein translation from a desired RNA, a 5'-cap molecule such as m7GpppN can be added in the 5' of 5'-end RdRp-binding site and at least a Kozak sequence can be added between the 5'-end RdRp-binding site and the coding region of the desired RNA/mRNA. Due to our recent findings and further designs of these novel RdRp-binding sites, the currently available coronaviral (COVID-19) and HCV RdRp enzymes can be used to efficiently synthesize and amplify either the sense (+) or antisense (−) strands, or both, of desired samRNA sequences in vitro, ex vivo as well as in vivo.

Both 5'-end and 3'-end RdRp-binding sites are required for the cycling reaction of RCR-mediated samRNA amplification. As a result, the resulting samRNA products amplified by RCR methods are all in full-length conformation. Notably, the samRNA templates and the resulting samRNA products may contain the same or different 5'-end and 3'-end RdRp-binding sites. Also, the samRNA templates and the resulting ssamRNAs may contain single or multiple 5'-end and/or 3'-end RdRp-binding sites, respectively. The 5'-end and 3'-end RdRp-binding sites can be complementary to each other and their complementarity can be partial (>57%~99%) or perfect (100%) match to each other. Noteworthily, the combination of multiple 5'-end and/or 3'-end RdRp-binding sites can further enhance the samRNA amplification efficiency of replicase/RdRp enzymes. Theoretically, the newly synthesized samRNAs and the samRNA templates may form a double-stranded RNA (dsRNA) conformation, which may also enhance RCR-mediated amplification as well. Hence, the starting samRNA templates can be in either single- or double-stranded conformation, or a combination thereof.

In view of our prior studies and the present invention, it clearly shows the differences between the present invention and the previous Ahn's and Bloom's findings. Both Ahn and Bloom et al consider that their large intact, highly structured stem-loop binding sites are required to initiate RdRp activity, while our findings demonstrate that merely the right complementary pairs of 5'-end and 3'-end RdRp-binding sites are required, but not the whole loop structures. The large multiple loop structures can be removed or replaced by a smaller modified hairpin structure less than seven nucleotide base-pairs (<7-bp), without affecting the RdRp binding efficiency. In fact, our modifications can provide higher samRNA amplification efficiency than the prior Ahn's and Bloom's designs. Our studies indicate that the 5'- and 3'-end RdRp-binding sites form a complementary pair to stabilize the binding of RdRp on a desired samRNA template and then start a reaction cycle to activate the RNA synthesis of the reverse, complementary (antisense) strand RNAs and vice versa. Hence, any large loop structure in the 5'-end RdRp-binding site will disrupt and hinder the reaction cycle of samRNA synthesis. As a result, Ahn's and Bloom's methodologies can only provide a limited effect of 3'-end RNA extension of one strand, while the present invention successfully achieves multiple cycles of amplification of both sense (+) and antisense (−) strand RNAs.

As shown in the present invention and our priority invention U.S. patent application Ser. Nos. 17/648,336 and 17/648,340, the combinations of various 5'- and 3'-end RdRp-binding sites can provide different RNA/mRNA amplification rates, depending on the length and structural complexity of the desired samRNA sequences. Due to such a variety of different RdRp-binding site combinations, we can selectively amplify one RNA strand over the other strand or one kind of RNA strands over the other kind of RNA strands. By this means, a relatively pure single-stranded and/or double-stranded samRNA products of the desired RNA/mRNA sequences can be generated, obtained and collected in RCR and then further purified by other methodologies.

In one preferred embodiment, the desired RNA sequence (i.e, mRNA or microRNA, or any other kind of RNA species) contains at least an RdRp-binding site in both of its 5'- and 3'-end regions. Since both ends of the desired RNA carry at least an RdRp-binding site for RNA amplification with replicase/RdRp activities, the sense-strand RNA sequences can be used to amplify its complementary, antisense-strand (−) RNAs (cRNA or aRNA), while the antisense-strand RNA sequences can be used to amplify the sense-strand (+) RNAs as well, so as to form an amplification cycle of both of the sense- and antisense-strand RNAs and thus resulting in a maximal amplification rate of the desired RNAs. The desired RNAs so obtained can be in either single-stranded or double-stranded conformation, depending on the use of RdRp-binding site combinations in the sequence ends and the stop point of RCR. Also, the resulting sense- and antisense-strand RNAs may further form double-stranded RNAs, facilitating the generation of siRNAs, shRNAs, miRNAs, and/or piRNAs of the desired RNA sequences.

Alternatively, in another preferred embodiment, the desired RNA sequence contains at least an RdRp-binding site in its either 5'-end or 3'-end region. In this way, we can selectively amplify either the sense- or antisense-strand of the desired RNA, leading to more specific amplification of the desired RNA strand. Particularly, this approach is useful for generating and amplifying either the mRNA or the antisense RNA (aRNA) of a specific functional protein, viral antigen or antibody, facilitating the development of mRNA vaccines and/or RNA/antibody-based medicines. Notably, these resulting mRNA vaccines and RNA/antibody-based medicines of the present invention are kinds of pharmaceutical compositions useful for treating a variety of human diseases, including but not limited to Alzheimer's disease, Parkinson's disease, motor neuron disease, stroke, diabetes, myocardial infraction, hemophilia, anemia, leukemia, and many kinds of cancers as well as many kinds of viral and bacterial infections.

Conceivably, our new RCR methodology can be used to produce and amplify a variety of RNA species carrying at least an RdRp binding site, particularly viral antigen mRNAs and/or known functional RNAs/mRNAs, which are useful for developing anti-viral and/or anti-disease vaccines as well as medicines, and likely many more. For example, as shown in our priority U.S. patent application Ser. Nos. 17/489,357 and 17/648,336, we had developed several new samRNA concepts and designs for generating novel mRNA vaccines as well as medicines for treating viral infections and cancers, respectively. Alternatively, by co-transfection of RCR-ready samRNA templates and an isolated corona-viral RdRp mRNA into human somatic cells, our US priority patent application Ser. No. 17/648,340 had demonstrated a novel method for inducing iPS cell generation. Moreover, the RCR-amplified mRNAs can be further used in an in-vitro translation system for producing the encoded proteins, peptides and/or antibodies of interest. In view of these prior proof-of-principle achievements, the development of many more potential applications of the present invention are highly expected.

In case of producing highly structured samRNA templates, our claimed priority U.S. patent application Ser. No. 17/489,357 had developed another novel PCR-IVT methodology for overcoming the low efficiency problem of highly structured RNA/mRNA generation. Traditionally, it is not reasonable for an ordinary skill person in the art to anticipate the effective generation of highly structured RNAs in vitro because it is known that the presence of hairpin- and/or stem-loop-like RNA structures greatly hinders RNA transcription. In fact, hairpin-like stem-loop structures are signals of intrinsic transcription termination for prokaryotic RNA polymerases (McDowell et al, Science 266:822-825, 1994). To solve this problem, our priority method adopts a new IVT system with a mixture of RNA polymerase and helicase activities. The additional helicase activity used in IVT (and likely in RCR as well) markedly reduces the secondary structures of both DNA/RNA templates and their resulting RNA products for far more efficiently producing highly structured RNAs. Accordingly, an improved buffer system is also used to maintain and enhance the efficiency of mixed RNA polymerase/replicase and helicase activities in IVT (and RCR as well). Interestingly, although several prior studies had reported that helicase may be involved in prokaryotic transcription termination, our studies however demonstrate a different functionality of helicase in RNA amplification during IVT (and IVT-RCR as well).

For facilitating intracellular delivery/transfection in vitro, ex vivo or in vivo, the RCR-ready samRNA template(s) and RdRp mRNA, together or separately, can be mixed, conjugated, encapsulated and/or formulated with at least a delivery/transfection agent selected from, but not limited to, glycylglycerin-derived chemicals, liposomes, nanoparticles, liposomal nanoparticles (LNP), conjugating molecules, infusion/transfusion agents, gene gun materials, electroporation agents, transposons/retrotransposons, and a combination thereof.

The advantages of using RCR-amplified samRNA vaccines and medicines include (1) high RNA yield rate, (2) high full-length integrity, (3) high RNA purity without DNA contamination, (4) long-lasting efficacy, (5) simple production procedure compatible with other RT-PCR and IVT methods, (6) simple equipment requirement using either a PCR machine or a temperature-controlled incubator, and (7) a variety of potential applications developed. Hence, it is conceivable that the RCR-amplifiable samRNA of the present invention are extremely useful for designing and developing all kinds of desired RNA/mRNA medicines as well as vaccines for treating all varieties of human diseases, including but not limited to Alzheimer's disease, Parkinson's disease, motor neuron disease, stroke, diabetes, myocardial infraction, hemophilia, anemia, leukemia, and many kinds of cancers as well as many kinds of viral and bacterial infections. Clearly, a whole new field of nucleic acid medicine is developed and established based on the RCR and its related samRNA technologies of the present invention.

A. Definitions

To facilitate understanding of the invention, a number of terms are defined below:

Nucleic Acid: a polymer of deoxyribonucleic acid (DNA) or ribonucleic acid (RNA), either single or double stranded.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Deoxyribonucleoside Triphosphates (dNTPs): the building block molecules for DNA synthesis, including dATP, dGTP, dCTP, and dTTP and sometimes may further containing some modified deoxyribonucleotide analogs.

Ribonucleoside Triphosphates (rNTPs): the building block molecules for RNA synthesis, including ATP, GTP, CTP, and UTP and sometimes may further containing pseudouridine, 5'methyluridine, methoxyuridine, and/or some other modified ribonucleotide analogs.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Oligonucleotide: a molecule comprised of two or more monomeric units of DNA and/or RNA, preferably more than three, and usually more than ten. An oligonucleotide longer than 13 nucleotide monomers is also called polynucleotide.

The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (e.g. spliceosomes) and served as a protein-coding RNA for peptide/protein synthesis. Structurally, mRNA sequence may comprise 5'-cap nucleotide [such as m7G(5')ppp(5')N-], 5'-untranslated region (5'-UTR), at least a Kozak consensus translation initiation site (e.g., 5'-GCCACC-3'), at least a protein/peptide-coding region, polyadenylation signals (e.g. 5'-AUAAA-3' or 5'-AUUAAA-3'), and/or 3'-UTR with or without poly(A) tail. The proteins/peptides encoded by mRNAs include, but not limited to, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding. For example, a sense nucleotide sequence "5'-A-T-C-G-U-3'" can form complete base pairing with its antisense sequence "5'-A-C-G-A-T-3'".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, RNA or DNA, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double-stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3'" is complementary to not only the sequence "5'-A-C-T-3'" but also to "5'-A-C-U-3'". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with expression of intracellular genes containing either completely or partially complementarity to the small RNAs.

MicroRNA (miRNA): single-stranded RNAs capable of binding to targeted gene transcripts that have partial complementarity to the miRNA. MiRNA is usually about 17-27 oligonucleotides in length and is able to either directly degrade its intracellular mRNA target(s) or suppress the protein translation of its targeted mRNA, depending on the complementarity between the miRNA and its target mRNA. Natural miRNAs are found in almost all eukaryotes, functioning as a defense against viral infections and allowing regulation of gene expression during development of plants and animals.

Precursor MicroRNA (Pre-miRNA): hairpin-like single-stranded RNAs containing stem-arm and stem-loop regions for interacting with intracellular RNaseIII endoribonucleases to produce one or multiple microRNAs (miRNAs) capable of silencing a targeted gene or genes complementary to the microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation. In the present invention, however, precursor of microRNA may also includes pri-miRNA.

Small interfering RNA (siRNA): short double-stranded RNAs sized about 18-27 perfectly base-paired ribonucleotide duplexes and capable of degrading target gene transcripts with almost perfect complementarity.

Small or short hairpin RNA (shRNA): single-stranded RNAs that contain a pair of partially or completely matched stem-arm nucleotide sequences divided by an unmatched loop or bubble oligonucleotide to form a hairpin-like structure. Many natural miRNAs are derived from small hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site (such as 5'-GCCACC-3'), polyadenylation signals (such as 5'-AUAAA-3' or 5'-AUUAAA-3'), a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, perhaps binds to, and initiates RNA transcription. For the purposes of the instant invention, a promoter can be a known polymerase binding site, an enhancer and the like, any sequence that can initiate synthesis of RNA transcripts by a desired polymerase.

RNA Processing: a cellular mechanism responsible for RNA maturation, modification and degradation, including RNA splicing, intron excision, exosome digestion, nonsense-mediated decay (NMD), RNA editing, RNA processing, 5'-capping, 3'-poly(A) tailing, and a combination thereof.

Gene Delivery: a genetic engineering method selected from the group consisting of polysomal transfection, liposomal transfection, chemical (nanoparticle) transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Transfected Cell: a single or a plurality of eukaryotic cells after being artificially inserted with at least a nucleic acid sequence or protein/peptide molecule into the cell(s), selected from the group consisting of a somatic cell, a tissue cell, a stem cell, a germ-line cell, a tumor cell, a cancer cell, a virus-infected cell, and a combination thereof.

Antibody: a peptide or protein molecule having a pre-selected conserved domain structure coding for a receptor capable of binding a pre-selected ligand.

Pharmaceutical and/or therapeutic Application: a biomedical utilization and/or apparatus useful for stem cell generation, drug/vaccine development, non-transgenic gene therapy, cancer therapy, disease treatment, wound healing, tissue/organ repair and regeneration, and high-yield production of proteins/peptides/antibodies, drug ingredients, medicines, vaccines and/or food supplies, and a combination thereof.

B. Compositions and Applications

A novel composition of self-amplifying RNA (samRNA), comprising:

At least a desired RNA sequence flanked with at least a 5'-end RdRp-binding site and at least a 3'-end RdRp-binding site; wherein said 5'- and 3'-end RdRp-binding sites are isolated or modified from the RNA-dependent RNA polymerase (RdRp)-binding sites of coronaviral COVID-19 virus or hepatitis C virus (HCV). Notably, the desired RNA can be any protein/peptide/antibody-coding mRNA or non-coding siRNA/shRNA/microRNA (miRNA)/pre-miRNA, or a combination thereof. Also, the desired RNA can be in either single-stranded or double-stranded conformation, or a mixture (e.g. shRNA or pre-miRNA) thereof. For increasing RNA stability, the uridine/uracil (U) contents of the desired RNA and its derived samRNA products can be totally or partially replaced by pseudouridine, 5-methyluridine, 5-methoxyuridine, or other modified nucleotide analogs. Moreover, the desired RNA may comprise a 5'-end cap molecule, such as m7G(5')ppp(5')N and/or its analogs. Furthermore, the desired RNA may comprise at least a Kozak motif sequence for facilitating protein/peptide translation.

For samRNA amplification with coronaviral (e.g. COVID-19) and/or HCV-derived RdRp, the 5'-end RdRp-binding site of samRNA contains at least a consensus sequence homologous or complementary to 5'-AU(G/C)(U/-)G(A/U)-3' (i.e. 5'-AUSUGW-3'; SEQ ID NO:1) or 5'-U(C/-)(U/A)C(U/C)(U/A)A-3' (i.e. 5'-UCWCYWA-3'; SEQ ID NO:2), or both, while the 3'-end RdRp-binding site contains at least a consensus sequence homologous or complementary to 5'-(U/A)C(A/-)(C/G)AU-3' (i.e. 5'-WCA-SAU-3'; SEQ ID NO:3) or 5'-U(A/U)(A/G)G(A/U)(G/-)A-3' (i.e. 5'-UWRGWR-3'; SEQ ID NO:4), or both. Preferably, the 5'-end RdRp-binding site contains at least a sequence of 5'-AUCUGU-3' (SEQ ID NO:5), 5'-UCUCUAA-3' (SEQ ID NO:6), 5'-UCUCCUA-3' (SEQ ID NO:7), and/or 5'-UU-CAA-3' (SEQ ID NO:8), or a combination thereof, while the 3'-end RdRp-binding site contains at least a sequence of 5'-ACAGAU-3' (SEQ ID NO:9), 5'-UUAGAGA-3' (SEQ ID NO:10), 5'-UAGGAGA-3' (SEQ ID NO:11), and/or 5'-UUGAA-3' (SEQ ID NO:12), or a combination thereof. Also, these RdRp-binding sites can be used together to form a combination, so as to further enhancing the related RCR activity in vitro, ex vivo as well as in vivo. Notably, in these RdRp-binding sites, the contents of uracil (U) and thymine (T) are mutually exchangeable, depending on various DNA and/or RNA construct designs. For incorporating the RdRp-binding sites into PCR primers, the uridine/uracil (U) contents of these RdRp-binding sites can be replaced by thymidine (dT) and/or deoxyuridine (dU) in the primers.

BRIEF DESCRIPTION OF THE DRAWINGS

Referring particularly to the drawings for the purpose of illustration only and not limitation, there is illustrated.

Then, a part or whole procedure of this novel RCR method is used to produce and amplify the desired RNA sequences from the RCR-ready cDNA/samRNA templates after single or multiple cycle amplification. Alternatively, since IVT and RCR methods can be performed simultaneously under the same buffer condition, the RCR-ready cDNA/samRNA templates can also be used as starting materials for amplifying the desired RNA sequences in a combined IVT-RCR reaction.

Figure 1:
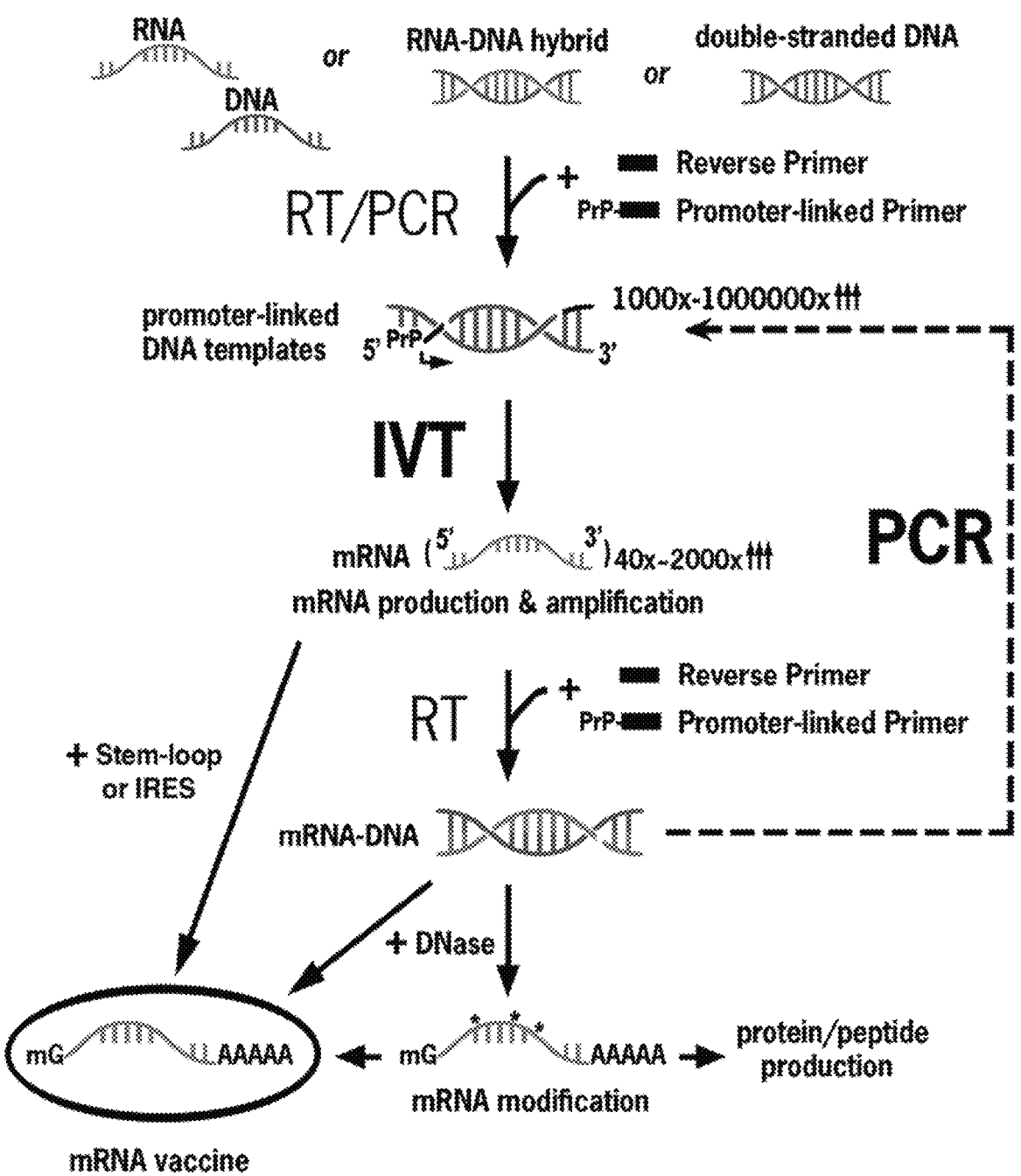
FIG. 1 depicts the step-by-step procedure of the prior PCR-IVT methodology. For RNA production, a part or whole procedure of this PCR-IVT method can be adopted for either single or multiple cycle amplification of desired RNA products.
Figure 2:
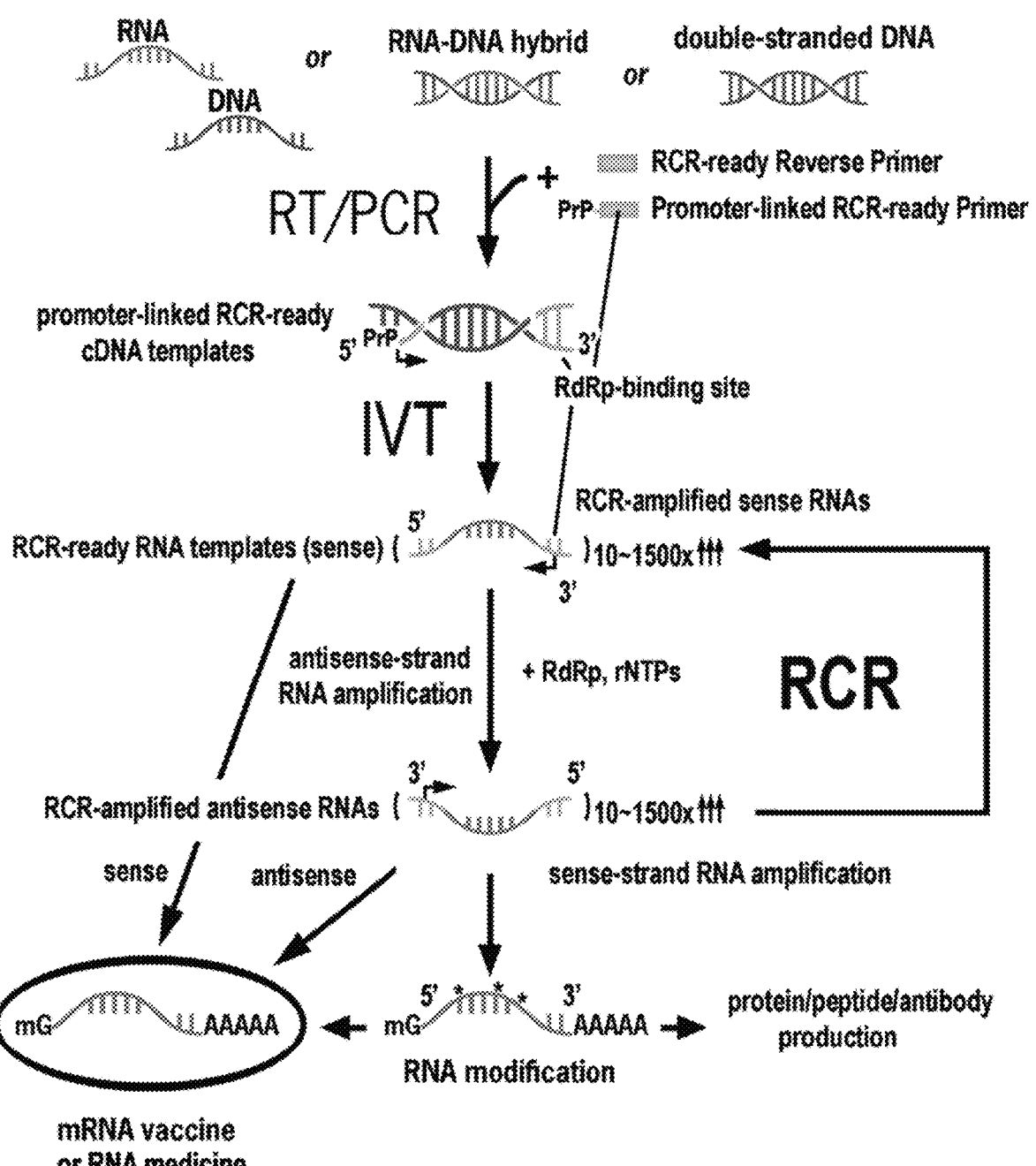
FIG. 2 depicts the step-by-step procedure of the presently invented RCR methodology. For preparing RCR-ready cDNA and/or samRNA templates, at least a coronaviral and/or HCV replicase/RdRp-binding site is incorporated into the 5'- or 3'-ends, or both, of the cDNAs of desired RNA sequences, using conventional RT-PCR or PCR methods.
Figure 3:
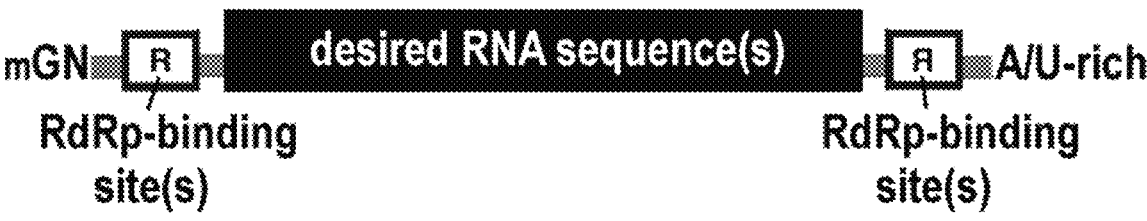

FIG. 3 depicts the designed structures of RCR-ready cDNA/samRNA templates. It is noted that the RCR-ready cDNA templates are in double-stranded DNA conformation (useful for IVT and combined IVT-RCR reactions), while the RCR-ready samRNA templates are in single-stranded RNA conformation (useful for RCR). For further enhancing the stability of RCR-ready samRNA templates, the uridine/uracil (U) contents of the templates can be replaced by pseudouridine, 5-methyluridine, methoxyuridine, or other modified nucleotide analogs.

Figure 4:
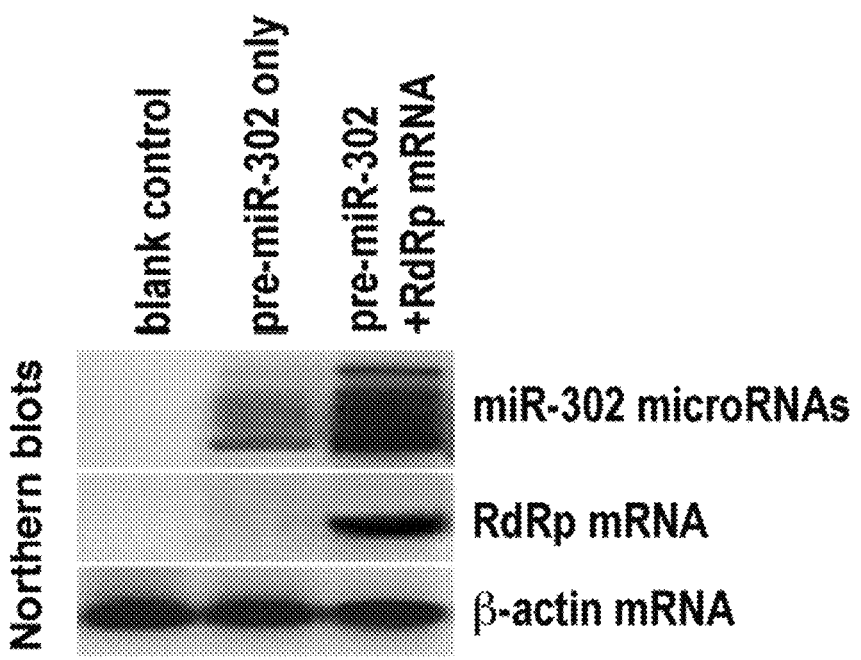

FIG. 4 shows the Northern blot analysis results of markedly increased expressions of miR-302 microRNAs (i.e. from top to bottom: b, c, d, a) and RdRp mRNA (e.g. HCV NS5B or modified COVID-19 NSP12) in transfected human cells after co-transfection with RCR-ready miR-302 precursor microRNA (pre-miR-302) samRNA and viral RdRp mRNA templates (as shown in most right) compared to the result of cells transfected with only the pre-miR-302 samRNA template (in middle), demonstrating the evidence of RCR-mediated amplification in the transfected cells.

Figure 5:
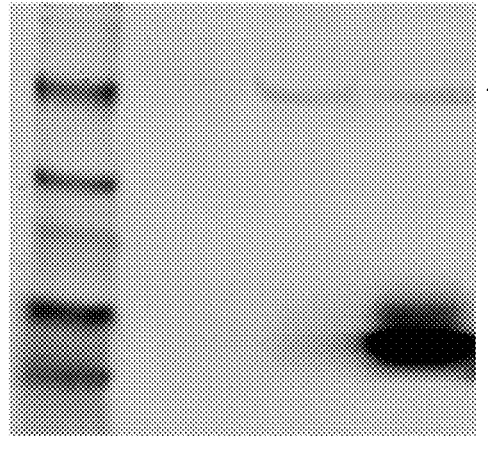

FIG. 5 shows Northern blot analysis results of RCR-ready cDNA and samRNA templates as well as the resulting samRNA products (i.e. samRNA sequences containing viral antigen proteins/peptides) amplified by RdRp enzymes in an in-vitro IVT-RCR reaction, demonstrating the evidence of RCR in vitro.

Figure 6:
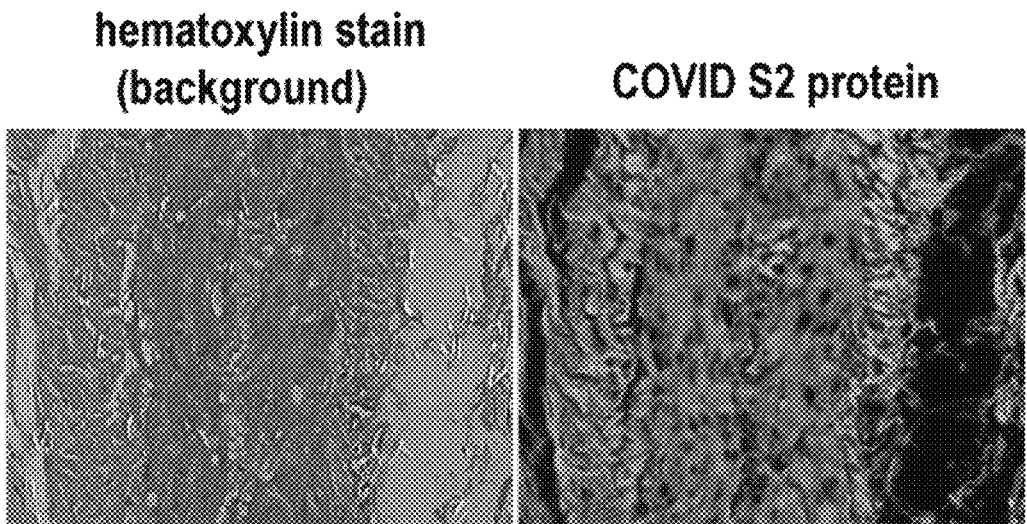

FIG. 6 shows the immunohistochemical staining of coronaviral (e.g. COVID-19) S 2 proteins produced in the mouse muscle cells in vivo after co-transfection with RCR-amplified S protein samRNA (from FIG. 5) and isolated RdRp mRNA (from FIG. 4), indicating that the present invention is useful for developing and manufacturing anti-viral mRNA vaccines.

EXAMPLES

1. Human Cell Isolation and Cultivation

Starting tissue cells can be obtained from either enzymatically dissociated skin cells using Aasen's protocol (Nat. Protocols 5, 371-382, 2010) or simply from the buffy coat fraction of heparin-treated peripheral blood cells. The isolated tissue samples must be kept fresh and used immediately by mixing with 4 mg/mL collagenase I and 0.25% TrypLE for 15-45 min, depending on cell density, and rinsed by HBSS containing trypsin inhibitor two times and then transferred to a new sterilized microtube containing 0.3 mL of feeder-free SFM culture medium (IrvineScientific, CA). After that, cells were further dissociated by shaking in a microtube incubator for 1 min at 37° C. and then transferred the whole 0.3 mL cell suspension to a 35-mm Matrigel-coated culture dish containing 1 mL of feeder-free SFM culture medium supplemented with formulated pre-miR-302+RdRp mRNA mixture, LIF, and bFGF/FGF2, or other optional defined factors. The concentrations of pre-miR-302+RdRp mRNA mixture, LIF, bFGF/FGF2, and other optional defined factors are ranged from 0.1 to 500 microgram (μg)/mL, respectively, in the cell culture medium. The cell culture medium and all of the supplements must be refreshed every 2-3 days and the cells are passaged at about 50%~60% confluence by exposing the cells to trypsin/ EDTA for 1 min and then rinsing two times in HBSS containing trypsin inhibitor. For ASC expansion, the cells were replated at 1:5-1:500 dilution in fresh feeder-free MSC Expansion SFM culture medium supplemented with formulated pre-miR-302+RdRp mRNA mixture, LIF, bFGF/ FGF2, and/or other optional defined factors. For culturing keratinocytes, cells are isolated from skin tissues and cultivated in EpiLife serum-free cell culture medium supplemented with human keratinocyte growth supplements (HKGS, Invitrogen, Carlsbad, CA) in the presence of proper antibiotics at 37° C. under 5% $CO_2$. Culture cells are passaged at 50%-60% confluency by exposing cells to trypsin/EDTA solution for 1 min and rinsing once with phenol red-free DMEM medium (Invitrogen), and the detached cells are replated at 1:10 dilution in fresh EpiLife medium with HKGS supplements. Human cancer and normal cell lines A549, MCF7, PC3, HepG2, Colo-829 and BEAS-2B were obtained either from the American Type Culture Collection (ATCC, Rockville, MD) or our collaborators and then maintained according to manufacturer's or provider's suggestions. After reprogramming, the resulting iPS cells (iPSCs) were cultivated and maintained following either Lin's feeder-free or Takahashi's feeder-based iPSC culture protocols (Lin et al., RNA 14:2115-2124, 2008; Lin et al., *Nucleic Acids Res.* 39:1054-1065, 2011; Takahashi K and Yamanaka S, *Cell* 126:663-676, 2006).

2. In-Vitro RNA Transfection

For intracellular delivery/transfection, 0.5-200 µg of RCR-amplified RNA/mRNA (i.e. pre-miR-302 or coronaviral S protein mRNA) and RdRp mRNA mixture (ratio ranged from about 20:1 to 1:20) is dissolved in 0.5 ml of fresh cell culture medium and mixed with 1-50 µl of In-VivoJetPEI or other similar transfection reagents. After 10~30 min incubation, the mixture is then added into a cell culture containing 50%-60% confluency of the cultivated cells. The medium is reflashed every 12 to 48 hours, depending on cell types. This transfection procedure may be performed repeatedly to increase transfection efficiency.

3. Preparation of RCR-Ready cDNA/samRNA Templates

Reverse transcription (RT) of desired RNA/mRNA is performed by adding about 0.01 ng-10 microgram (µg) of isolated RNA/mRNA into a 20-50 µL RT reaction (SuperScript III cDNA RT kit, ThermoFisher Scientific, MA, USA), following the manufacturer's suggestions. Depending on the RNA/mRNA amount, the RT reaction mixture further contains about 0.01-20 nmole RT primer, a proper amount of deoxyribonucleoside triphosphate molecules (dNTPs) and reverse transcriptase in 1×RT buffer. Then, the RT reaction is incubated at 37-65° C. for 1-3 hours (hr), depending on the length and structural complexity of the desired RNA/mRNA sequences, so as to make the complementary DNA (cDNA) templates thereof for the next step of PCR. For isolation of viral RdRp mRNA, we have designed and used an RT-reverse primer 5'-GACAACAGGT GCGCTCAGGT CCT-3' (SEQ ID NO: 13) to generate the coronaviral RdRp cDNA sequence, which already possesses internal motif sequences similar to SEQ ID NO:9.

Next, polymerase chain reaction (PCR) is performed by adding about 0.01 pg-10 µg of the RT-derived cDNAs into a 20-50 µL PCR preparation mixture (High-Fidelity PCR master kit, ThermoFisher Scientific, MA, USA), following the manufacturer's suggestions. Then, the PCR mixture is first incubated in five to twenty (5-20) cycles of denaturation at 94° C. for 1 mim, annealing at 30-55° C. for 30 sec-1 min, and then extension at 72° C. for 1-3 min, depending on the structure and length of the desired cDNA sequences. After that, another ten to twenty (10-20) cycles of PCR are performed with a series of sequential cycling steps of denaturation at 94° C. for 1 mim, annealing at 50-58° C. for 30 sec, and then extension at 72° C. for 1-3 min, depending on the structure and length of the resulting PCR products. Finally, the resulting PCR products are used as cDNA templates for IVT and RCR. For IVT-RCR template preparation, we design and use a specific pair of RCR-ready PCR primers for incorporating the identified RdRp-binding sites into the PCR-derived RdRp cDNA templates, including SEQ ID NO: 13 and 5'-GATATCTAAT ACGACTCACT ATAGGGAGAG GTATGGTACT TGGTAGTT-3' (SEQ ID NO:14). Later, a 5'-cap molecule, such as m7G(5')ppp(5')N and/or its analogs, may be further incorporated in the resulting mRNA products of IVT-RCR or RCR. On the other hand, we also design and use another pair of RCR-ready PCR primers for incorporating the identified RdRp-binding sites into the PCR-derived cDNA templates of human pre-miR-302 familial cluster (pre-miR-302), including 5'-GA-TATCTAAT ACGACTCACT ATAGGGAGAT CTGTGG-GAAC TAGTTCAGGA AGGTAA-3' (SEQ ID NO:15) and 5'-GTTCTCCTAA GCCTGTAGCC AAGAACTGCA CA-3' (SEQ ID NO:16). In the current primer designs, various sequences and different combinations of RNA promoters and/or RdRp-binding sites can also be used, such as T7, T3, M13 and/or SP6 promoter, and at least an RdRp binding site must be incorporated in the 5'-end or 3'-end primers, or both.

For generating RCR-ready samRNA templates, since at least a promoter and at least an RdRp-binding site have been incorporated into the resulting PCR-derived cDNA products (served as RCR-ready cDNA templates), an IVT-RCR reaction can then be performed to amplify desired samRNA sequences from the cDNA templates. The IVT-RCR reaction mixture contains 0.01 ng~10 µg of the PCR-derived cDNA product, 0.1-50 U of isolated coronaviral RdRp/helicase (Abcam, MA, USA/Creative Enzymes, NY), a proper amount of ribonucleoside triphosphate molecules (rNTPs) and RNA polymerase (i.e. T7, T3, M13 and/or SP6) in 1× transcription buffer. The transcription buffer is commercially available and may be further adjusted according to the manufacturer's suggestions. Preferably, the 1× transcription buffer may further contain 0.001~10 mM of betaine (trimethylglycine, TMG), dimethylsulfoxide (DMSO), and/or 3-(N-morpholino)propane sulfonic acid (MOPS), and/or a combination thereof. Then, the IVT-RCR reaction is incubated at 30-40° C. for 1-6 hr, depending on the stability and activity of the used RdRp and RNA polymerase enzymes.

4. Novel RCR Protocol

The starting RCR mixture contains about 0.01 ng-10 µg of the RCR-ready samRNA templates, about 0.1-50 U of isolated coronaviral RdRp/helicase, and a proper amount of rNTPs in 1× transcription buffer. RdRp/helicase is either an RdRp enzyme with an additional RNA unwinding activity or a mixture of RdRp and helicase. The transcription buffer is commercially available in the market and may be further adjusted according to the manufacturer's suggestions. Additionally, the 1× transcription buffer may further contain 0.001~10 mM of betaine (trimethylglycine, TMG), dimethylsulfoxide (DMSO), and/or 3-(N-morpholino)propane sulfonic acid (MOPS), and/or a combination thereof, which facilitates the denaturation of highly structured RNA/DNA sequences, such as hairpins and stem-loop structures. After that, the RCR reaction is incubated at 20-45° C. for 1-6 hr, depending on the stability and activity of the used RdRp enzymes.

17 18

5. RNA Purification and Northern Blot Analysis

Desired RNAs (10 µg) are isolated with a mirVana™ RNA isolation kit (Ambion, Austin, TX) or similar purification filter column, following the manufacturer's protocol, and then further purified by using either 5%~10% TBE-urea polyacrylamide or 1%~3.5% low melting point agarose gel electrophoresis. For Northern blot analysis, the gel-fractionated RNAs are electroblotted onto a nylon membrane. Detection of the RNA and its IVT template (the PCR-derived cDNA product) is performed with a labeled [LNA]-DNA probe complementary to a target sequence of the desired RNA. The probe is further purified by high-performance liquid chromatography (HPLC) and tail-labeled with terminal transferase (20 units) for 20 min in the presence of either a dye-labeled nucleotide analog or [$^{32}$P]-dATP (>3000 Ci/mM, Amersham International, Arlington Heights, IL).

6. Protein Extraction and Western Blot Analysis

Cells ($10^6$) are lysed with a CelLytic-M lysis/extraction reagent (Sigma) supplemented with protease inhibitors, Leupeptin, TLCK, TAME and PMSF, following the manufacturer's suggestion. Lysates are centrifuged at 12,000 rpm for 20 min at 4° C. and the supernatant is recovered. Protein concentrations are measured using an improved SOFTmax protein assay package on an E-max microplate reader (Molecular Devices, CA). Each 30 µg of cell lysate are added to SDS-PAGE sample buffer under reducing (+50 mM DTT) and non-reducing (no DTT) conditions, and boiled for 3 min before loading onto a 6~8% polyacylamide gel. Proteins are resolved by SDS-polyacrylamide gel electrophoresis (PAGE), electroblotted onto a nitrocellulose membrane and incubated in Odyssey blocking reagent (Li-Cor Biosciences, Lincoln, NB) for 2 hr at room temperature. Then, a primary antibody is applied to the reagent and incubated the mixture at 4° C. After overnight incubation, the membrane is rinsed three times with TBS-T and then exposed to goat anti-mouse IgG conjugated secondary antibody to Alexa Fluor 680 reactive dye (1:2,000; Invitrogen-Molecular Probes), for 1 hr at the room temperature. After three additional TBS-T rinses, fluorescent scanning of the immunoblot and image analysis are conducted using Li-Cor Odyssey Infrared Imager and Odyssey Software v. 10 (Li-Cor).

7. Immunostaining Assay

Cell/Tissue samples are fixed in 100% methanol for 30 min at 4° C. and then 4% paraformaldehyde (in 1×PBS, pH 7.4) for 10 min at 20° C. After that, the samples are incubated in 1×PBS containing 0.1%~0.25% Triton X-100 for 10 min and then washed in 1×PBS three times for 5 min. For immunostaining, primary antibodies were purchased from Invitrogen (CA, USA) and Sigma-Aldrich (MO, USA), respectively. Dye-labeled goat anti-rabbit or horse anti-mouse antibody are used as the secondary antibody (Invitrogen, CA, USA). Results are examined and analyzed at 100× or 200× magnification under a fluorescent 80i microscopic quantitation system with a Metamorph imaging program (Nikon).

8. In Vivo Transfection Assay

The mixture of RCR-amplified samRNA and RdRp mRNA (ratio ranged from about 20:1 to 1:20) is mixed well with a proper amount of delivery agent, such as an In-VivoJetPEI transfection reagent or other similar LNP-based delivery/transfection agents, following the manufacturer's protocol, and then injected into blood veins or muscles of an animal, depending the purpose of applications. The delivery/transfection agent is used for mixing, conjugating, encapsulating or formulating the amplified samRNA and RdRp mRNA mixture, so as to not only protect the RNA contents from degradation but also facilitate the delivery/transfection of the samRNA and RdRp mRNA mixture into specific target cells of interest in vitro, ex vivo and/or in vivo.

9. Statistic Analysis

All data were shown as averages and standard deviations (SD). Mean of each test group was calculated by AVERAGE of Microsoft Excel. SD was performed by STDEV. Statistical analysis of data was performed by One-Way ANOVA. Tukey and Dunnett's t post hoc test were used to identify the significance of data difference in each group. $p < 0.05$ was considered significant (SPSS v 12.0, Claritas Inc).

REFERENCES

1. WO2002/092774 to Shi-Lung Lin et al.
2. U.S. Pat. No. 7,662,791 to Shi-Lung Lin et al.
3. U.S. Pat. No. 8,080,652 to Shi-Lung Lin et al.
4. U.S. Pat. No. 8,372,969 to Ying SY and Shi-Lung Lin.
5. U.S. Pat. No. 8,609,831 to Shi-Lung Lin and Ying SY.
6. Shi-Lung Lin and Ji H; cDNA library construction using in-vitro transcriptional amplification. Methods Mol Biol. 221:93-101, 2003.
7. Ahn et al.; Biochemical characterization of a recombinant SARS coronavirus nsp12 RNA-dependent RNA polymerase capable of copying viral RNA templates. Arch. Virol. 157:2095-2104, 2012.
8. Bloom et al; Self-amplifying RNA vaccines for infectious diseases. Gene Therapy 28:117-129, 2021.
9. McDowell et al.; Determination of intrinsic transcription termination efficiency by RNA polymerase elongation rate. Science 266:822-825, 1994.
10. Aasen et al.; Isolation and cultivation of human keratinocytes from skin or plucked hair for the generation of induced pluripotent stem cells. Nat. Protocols 5:371-382, 2010.
11. Shi-Lung Lin et al.; Mir-302 reprograms human skin cancer cells into a pluripotent ES-cell-like state. RNA 14:2115-2124, 2008.
12. Shi-Lung Lin et al.; Regulation of somatic cell reprogramming through inducible mir-302 expression. Nucleic Acids Res. 39:1054-1065, 2011.
13. Takahashi K and Yamanaka S; Induction of pluripotent stem cells from mouse embryonic and adult fibroblast cultures by defined factors. Cell 126:663-676, 2006.
14. Hillen et al.; Structure of replicating SARS-CoV-2 polymerase. Nature 584:154-159, 2020.

SEQUENCE LISTING

```
(1) GENERAL INFORMATION:

(iii) NUMBER OF SEQUENCES: 16

(2) INFORMATION FOR SEQ ID NO: 1:

(i) SEQUENCE CHARACTERISTICS:

(A) LENGTH: 6 base pairs (B) TYPE: nucleic acid (C) STRANDEDNESS: single (D) TOPOLOGY: linear
```

-continued

```
 (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 1:

AUSUGW (2) INFORMATION FOR SEQ ID NO: 2:

(i) SEQUENCE CHARACTERISTICS:

(A) LENGTH: 7 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 2:

UCWCYWA (2) INFORMATION FOR SEQ ID NO: 3:

(i) SEQUENCE CHARACTERISTICS:

(A) LENGTH: 6 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 3:

WCASAU (2) INFORMATION FOR SEQ ID NO: 4:

(i) SEQUENCE CHARACTERISTICS:

(A) LENGTH: 6 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO
```

-continued

```
 (iv) ANTI-SENSE: NO (xi) SEQUENCE DESCRIPTION: SEQ ID NO: 4:

UWRGWR (2) INFORMATION FOR SEQ ID NO: 5:

(i) SEQUENCE CHARACTERISTICS:

(A) LENGTH: 6 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 5:

AUCUGU (2) INFORMATION FOR SEQ ID NO: 6:

(i) SEQUENCE CHARACTERISTICS:

(A) LENGTH: 7 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 6:

UCUCUAA (2) INFORMATION FOR SEQ ID NO: 7:

(i) SEQUENCE CHARACTERISTICS:

(A) LENGTH: 7 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 7:

UCUCCUA
```

-continued

-continued (2) INFORMATION FOR SEQ ID NO: 8:

(i) SEQUENCE CHARACTERISTICS:

(A) LENGTH: 5 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 8:

UUCAA (2) INFORMATION FOR SEQ ID NO: 9:

(i) SEQUENCE CHARACTERISTICS:

(A) LENGTH: 6 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 9:

ACAGAU (2) INFORMATION FOR SEQ ID NO: 10:

(i) SEQUENCE CHARACTERISTICS:

(A) LENGTH: 7 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 10:

UUAGAGA (2) INFORMATION FOR SEQ ID NO: 11:

(i) SEQUENCE CHARACTERISTICS:

(A) LENGTH: 7 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 11:

UAGGAGA (2) INFORMATION FOR SEQ ID NO: 12:

(i) SEQUENCE CHARACTERISTICS:

(A) LENGTH: 5 base pairs (B) TYPE: nucleic acid (C) STRANDEDNESS: single (D) TOPOLOGY: linear (ii) MOLECULE TYPE: RNA (A) DESCRIPTION: /desc = "synthetic"

(iii) HYPOTHETICAL: NO (iv) ANTI-SENSE: NO (xi) SEQUENCE DESCRIPTION: SEQ ID NO: 12:

UUGAA (2) INFORMATION FOR SEQ ID NO: 13:

(i) SEQUENCE CHARACTERISTICS:

(A) LENGTH: 23 base pairs (B) TYPE: nucleic acid (C) STRANDEDNESS: single (D) TOPOLOGY: linear (ii) MOLECULE TYPE: DNA (A) DESCRIPTION: /desc = "synthetic"

(iii) HYPOTHETICAL: NO (iv) ANTI-SENSE: YES (xi) SEQUENCE DESCRIPTION: SEQ ID NO: 13:

GACAACAGGT GCGCTCAGGT CCT

-continued

-continued (2) INFORMATION FOR SEQ ID NO: 14:

(i) SEQUENCE CHARACTERISTICS:

(A) LENGTH: 48 base pairs (B) TYPE: nucleic acid (C) STRANDEDNESS: single (D) TOPOLOGY: linear (ii) MOLECULE TYPE: DNA (A) DESCRIPTION: /desc = "synthetic"

(iii) HYPOTHETICAL: NO (iv) ANTI-SENSE: NO (xi) SEQUENCE DESCRIPTION: SEQ ID NO: 14:

GATATCTAAT ACGACTCACT ATAGGGAGAG GTATGGTACT

TGGTAGTT (2) INFORMATION FOR SEQ ID NO: 15:

(i) SEQUENCE CHARACTERISTICS:

(A) LENGTH: 56 base pairs (B) TYPE: nucleic acid (C) STRANDEDNESS: single (D) TOPOLOGY: linear (ii) MOLECULE TYPE: DNA (A) DESCRIPTION: /desc = "synthetic"

(iii) HYPOTHETICAL: NO (iv) ANTI-SENSE: NO (xi) SEQUENCE DESCRIPTION: SEQ ID NO: 15:

GATATCTAAT ACGACTCACT ATAGGGAGAT CTGTGGGAAC

TAGTTCAGGA AGGTAA (2) INFORMATION FOR SEQ ID NO: 16:

(i) SEQUENCE CHARACTERISTICS:

(A) LENGTH: 32 base pairs (B) TYPE: nucleic acid (C) STRANDEDNESS: single (D) TOPOLOGY: linear (ii) MOLECULE TYPE: DNA (A) DESCRIPTION: /desc = "synthetic"

(iii) HYPOTHETICAL: NO (iv) ANTI-SENSE: YES (xi) SEQUENCE DESCRIPTION: SEQ ID NO: 16:

GTTCTCCTAA GCCTGTAGCC AAGAACTGCA CA

SEQUENCE LISTING

Sequence total quantity: 16
SEQ ID NO: 1          moltype =   length =
SEQUENCE: 1
000

SEQ ID NO: 2          moltype =   length =
SEQUENCE: 2
000

SEQ ID NO: 3          moltype =   length =
SEQUENCE: 3
000

SEQ ID NO: 4          moltype =   length =
SEQUENCE: 4
000

SEQ ID NO: 5          moltype =   length =
SEQUENCE: 5
000

SEQ ID NO: 6          moltype =   length =
SEQUENCE: 6
000

SEQ ID NO: 7          moltype =   length =
SEQUENCE: 7
000

SEQ ID NO: 8          moltype =   length =
SEQUENCE: 8
000

SEQ ID NO: 9          moltype =   length =

-continued

```
SEQUENCE: 9
000

SEQ ID NO: 10          moltype =   length =
SEQUENCE: 10
000

SEQ ID NO: 11          moltype =   length =
SEQUENCE: 11
000

SEQ ID NO: 12          moltype =   length =
SEQUENCE: 12
000

SEQ ID NO: 13          moltype = DNA  length = 23
FEATURE                Location/Qualifiers
source                 1..23
                       mol_type = other DNA
                       organism = synthetic construct
SEQUENCE: 13
gacaacaggt gcgctcaggt cct                                      23

SEQ ID NO: 14          moltype = DNA  length = 48
FEATURE                Location/Qualifiers
source                 1..48
                       mol_type = other DNA
                       organism = synthetic construct
SEQUENCE: 14
gatatctaat acgactcact atagggagag gtatggtact tggtagtt           48

SEQ ID NO: 15          moltype = DNA  length = 56
FEATURE                Location/Qualifiers
source                 1..56
                       mol_type = other DNA
                       organism = synthetic construct
SEQUENCE: 15
gatatctaat acgactcact atagggagat ctgtgggaac tagttcagga aggtaa   56

SEQ ID NO: 16          moltype = DNA  length = 32
FEATURE                Location/Qualifiers
source                 1..32
                       mol_type = other DNA
                       organism = synthetic construct
SEQUENCE: 16
gttctcctaa gcctgtagcc aagaactgca ca                            32
```

The invention claimed is:

1. A novel composition of self-amplifying RNA (samRNA), comprising:
   at least an isolated RNA sequence flanked with at least a 5'-end RdRp-binding site and at least a 3'-end RdRp-binding site, so as to form at least a samRNA platform construct;
   wherein said 5'-end RdRp-binding site contains a nucleotide sequence of UCWCYWA (SEQ ID NO: 2) and said 3'-end RdRp-binding site contains a nucleotide sequence of UWRGWR (SEQ ID NO: 4) and wherein said isolated RNA sequence is not a viral genome, wherein W comprises A/U; wherein Y comprises U/C; and wherein R comprises A/G.

2. The composition as defined in claim 1, wherein said 5'-end and 3'-end RdRp-binding sites contain over 57% complementarity to each other.

3. The composition as defined in claim 1, wherein said isolated RNA is single-stranded.

4. The composition as defined in claim 1, wherein said isolated RNA is double stranded.

5. The composition as defined in claim 1, wherein said isolated RNA contains modified nucleotide analogs.

6. The composition as defined in claim 1, wherein said isolated RNA is a pharmaceutical compound or composition.

7. The composition as defined in claim 1, wherein a plurality of said 5'-end and 3'-end RdRp-binding sites are used together in a combination.

8. The composition as defined in claim 1, wherein said isolated RNA is further formulated with at least a delivery agent for facilitating intracellular transfection.

9. The composition as defined in claim 8, wherein said delivery agent is liposomal nanoparticles (LNP).

10. The composition as defined in claim 1, wherein said samRNA is mRNA.

11. The composition as defined in claim 1, wherein said samRNA is precursor microRNA (pre-miRNA).

12. The composition as defined in claim 1, wherein said isolated RNA comprises a 5'-cap molecule.

13. The composition as defined in claim 1, wherein said isolated RNA comprises modified uridine nucleotides.

14. The composition as defined in claim 1, wherein said isolated RNA comprises at least a Kozak sequence.

* * * * *